(12) United States Patent
Meeks et al.

(10) Patent No.: US 7,554,654 B2
(45) Date of Patent: Jun. 30, 2009

(54) SURFACE CHARACTERISTIC ANALYSIS

(75) Inventors: Steven W. Meeks, Fremont, CA (US); Romain Sappey, San Diego, CA (US); Tom Carr, Leucadia, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 286 days.

(21) Appl. No.: 11/627,677

(22) Filed: Jan. 26, 2007

(65) Prior Publication Data

US 2008/0180656 A1 Jul. 31, 2008

(51) Int. Cl.
*G01N 21/00* (2006.01)

(52) U.S. Cl. ............... 356/237.2; 356/237.3; 356/237.4; 356/237.5; 356/237.6; 356/237.1

(58) Field of Classification Search .................... 356/73, 356/237.1–237.6, 338, 398, 335–343, 445–448, 356/369, 394; 250/559.01, 559.09, 559.16, 250/559.22, 227.26, 559.06

See application file for complete search history.

(56) References Cited

U.S. PATENT DOCUMENTS

| | | | |
|---|---|---|---|
| 2,593,189 A | 4/1952 | Rinia | |
| 4,378,159 A | 3/1983 | Galbraith | |
| 4,585,348 A | 4/1986 | Chastang | |
| 4,601,575 A | 7/1986 | Tamaki | |
| 4,650,333 A | 3/1987 | Crabb | |
| 4,794,264 A | 12/1988 | Quackenbos et al. | |
| 4,870,631 A | 9/1989 | Stoddard | |
| 4,873,430 A | 10/1989 | Juliana | |
| 4,905,311 A | 2/1990 | Hino et al. | |
| 4,999,510 A | 3/1991 | Hayano | |
| 5,017,012 A | 5/1991 | Merritt, Jr. et al. | |
| 5,067,817 A | 11/1991 | Glenn | |
| 5,125,741 A | 6/1992 | Okada | |
| 5,168,386 A | 12/1992 | Galbraith | |
| 5,189,481 A | 2/1993 | Jann | |
| 5,270,794 A | 12/1993 | Tsuji | |
| 5,392,116 A | 2/1995 | Makosh | |
| 5,416,594 A | 5/1995 | Gross et al. | |
| 5,565,979 A | 10/1996 | Gross | |
| 5,604,585 A | 2/1997 | Johnson et al. | |
| 5,608,527 A | 3/1997 | Valliant et al. | |
| 5,610,897 A | 3/1997 | Yamamoto | |
| 5,633,747 A | 5/1997 | Nikoonahad | |
| 5,644,562 A | 7/1997 | de Groot | |
| 5,737,085 A | 4/1998 | Zollars et al. | |
| 5,798,829 A | 8/1998 | Vaez-Iravani | |

(Continued)

FOREIGN PATENT DOCUMENTS

DE 4105192 8/1991

(Continued)

*Primary Examiner*—Gregory J Toatley, Jr.
*Assistant Examiner*—Tri T Ton
(74) *Attorney, Agent, or Firm*—Luedeka, Neely & Graham, P.C.

(57) ABSTRACT

In one embodiment, a system to measure defects on a surface of a wafer and an edge of the wafer using a single tool comprises a scatterometer to identify at least one defect region on the surface and a surface profile height measuring tool to measure one or more characteristics of the surface in the defect region with a surface profile height measuring tool.

2 Claims, 5 Drawing Sheets

U.S. PATENT DOCUMENTS

| | | | |
|---|---|---|---|
| 5,864,394 A | 1/1999 | Jordan, III et al. | |
| 5,880,838 A | 3/1999 | Marx et al. | |
| 5,883,714 A | 3/1999 | Jann et al. | |
| 5,898,500 A | 4/1999 | Canteloup et al. | |
| 5,903,342 A | 5/1999 | Yatsugake | |
| 5,963,314 A | 10/1999 | Worster et al. | |
| 5,985,680 A | 11/1999 | Singhal | |
| 5,986,763 A | 11/1999 | Inoue | |
| 5,995,226 A | 11/1999 | Abe | |
| 6,020,966 A | 2/2000 | Ausschnitt et al. | |
| 6,031,615 A | 2/2000 | Meeks | |
| 6,081,325 A | 6/2000 | Leslie | |
| 6,091,493 A | 7/2000 | Stover et al. | |
| 6,122,046 A | 9/2000 | Almogy | |
| 6,130,749 A | 10/2000 | Meeks | |
| 6,154,280 A | 11/2000 | Borden | |
| 6,169,601 B1 | 1/2001 | Eremin et al. | |
| 6,172,752 B1 | 1/2001 | Haruna et al. | |
| 6,198,533 B1 | 3/2001 | Meeks | |
| 6,229,610 B1 | 5/2001 | Meeks | |
| 6,268,919 B1 | 7/2001 | Meeks | |
| 6,392,749 B1 | 5/2002 | Meeks | |
| 6,433,877 B2 | 8/2002 | Watanabe et al. | |
| 6,515,745 B2 | 2/2003 | Vurens et al. | |
| 6,556,290 B2 | 4/2003 | Maeda et al. | |
| 6,603,541 B2 | 8/2003 | Lange | |
| 6,617,603 B2 | 9/2003 | Ishiguro et al. | |
| 6,624,884 B1 | 9/2003 | Imaino | |
| 6,624,894 B2 | 9/2003 | Olszak et al. | |
| 6,665,078 B1 | 12/2003 | Meeks | |
| 6,678,046 B2 | 1/2004 | Opsal | |
| 6,687,008 B1 | 2/2004 | Peale | |
| 6,690,473 B1 | 2/2004 | Stanke et al. | |
| 6,704,435 B1 | 3/2004 | Imaino | |
| 6,717,671 B1 | 4/2004 | Meeks | |
| 6,751,044 B1 | 6/2004 | Meeks | |
| 6,757,056 B1 | 6/2004 | Meeks et al. | |
| 6,781,103 B1 | 8/2004 | Lane | |
| 6,804,003 B1 | 10/2004 | Wang et al. | |
| 6,813,034 B2 | 11/2004 | Rosencwaig et al. | |
| 6,917,433 B2 | 7/2005 | Levy et al. | |
| 6,940,609 B2 | 9/2005 | Scheiner | |
| 6,956,660 B2 | 10/2005 | Meeks et al. | |
| 7,019,850 B2 | 3/2006 | Finarov | |
| 7,023,547 B2 | 4/2006 | Venkatasubbarao et al. | |
| 7,042,556 B1 | 5/2006 | Sun | |
| 7,042,577 B1 | 5/2006 | Jacob et al. | |
| 7,046,352 B1 | 5/2006 | Dayal et al. | |
| 7,075,630 B2 | 7/2006 | Meeks | |
| 7,113,284 B1 | 9/2006 | Meeks | |
| 7,161,683 B2 | 1/2007 | Weitzel | |
| 2002/0015146 A1 | 2/2002 | Meeks | |
| 2002/0107650 A1 | 8/2002 | Wack et al. | |
| 2002/0118359 A1 | 8/2002 | Fairley | |
| 2002/0145740 A1 | 10/2002 | Meeks | |
| 2002/0163634 A1 | 11/2002 | Meeks | |
| 2003/0025905 A1 | 2/2003 | Meeks | |
| 2003/0179370 A1 | 9/2003 | Goldberg et al. | |
| 2004/0017561 A1 | 1/2004 | Meeks | |
| 2004/0046959 A1 | 3/2004 | Meeks | |
| 2004/0130710 A1 | 7/2004 | Hwang et al. | |
| 2004/0160604 A1 | 8/2004 | Meeks | |
| 2004/0169850 A1 | 9/2004 | Meeks | |
| 2004/0233419 A1 | 11/2004 | Meeks | |
| 2005/0023491 A1 | 2/2005 | Young | |
| 2005/0057747 A1 | 3/2005 | Meeks | |
| 2005/0206888 A1 | 9/2005 | Yoshida et al. | |
| 2006/0072106 A1 | 4/2006 | Matsui et al. | |
| 2007/0030493 A1 | 2/2007 | Zettler et al. | |

FOREIGN PATENT DOCUMENTS

| | | |
|---|---|---|
| EP | 0080540 | 6/1983 |
| JP | 03085514 | 4/1991 |
| JP | 07055702 | 3/1995 |
| JP | 10325711 | 12/1998 |
| WO | WO9416310 | 7/1994 |

SURFACE CHARACTERISTIC ANALYSIS

RELATED APPLICATIONS

None

BACKGROUND

The subject matter described herein relates to surface character analysis techniques, and more particularly to thin film disk, semiconductor wafer or other rigid substrate inspection.

Semiconductor materials and magnetic storage materials may be inspected for defects such as, e.g., surface imperfections, particles, irregularities in the thickness of thin film coatings, and the like, which may hamper the performance of the material. Some inspection systems used to inspect magnetic media such as, e.g., disk drives use a mechanical glide process in which a piezoelectric sensor glides above a disk surface at a height of approximately 5 nanometers (nm) to detect asperities protruding from the surface.

The mechanical glide process suffers from several deficiencies. For example, the piezoelectric sensor only detects defects that protrude from the surface of the disk; it does not detect defects beneath the surface of the disk. In addition, the technique raises control issues. For example, it is difficult to control accurately the height of the piezoelectric sensor at a height of 5 nm. Further, the piezoelectric sensor suffers wear during use, and therefore must be replaced and recalibrated periodically.

Additional surface inspection techniques would find utility.

BRIEF DESCRIPTION OF THE DRAWINGS

The detailed description is described with reference to the accompanying figures.

DETAILED DESCRIPTION

Figure 1:
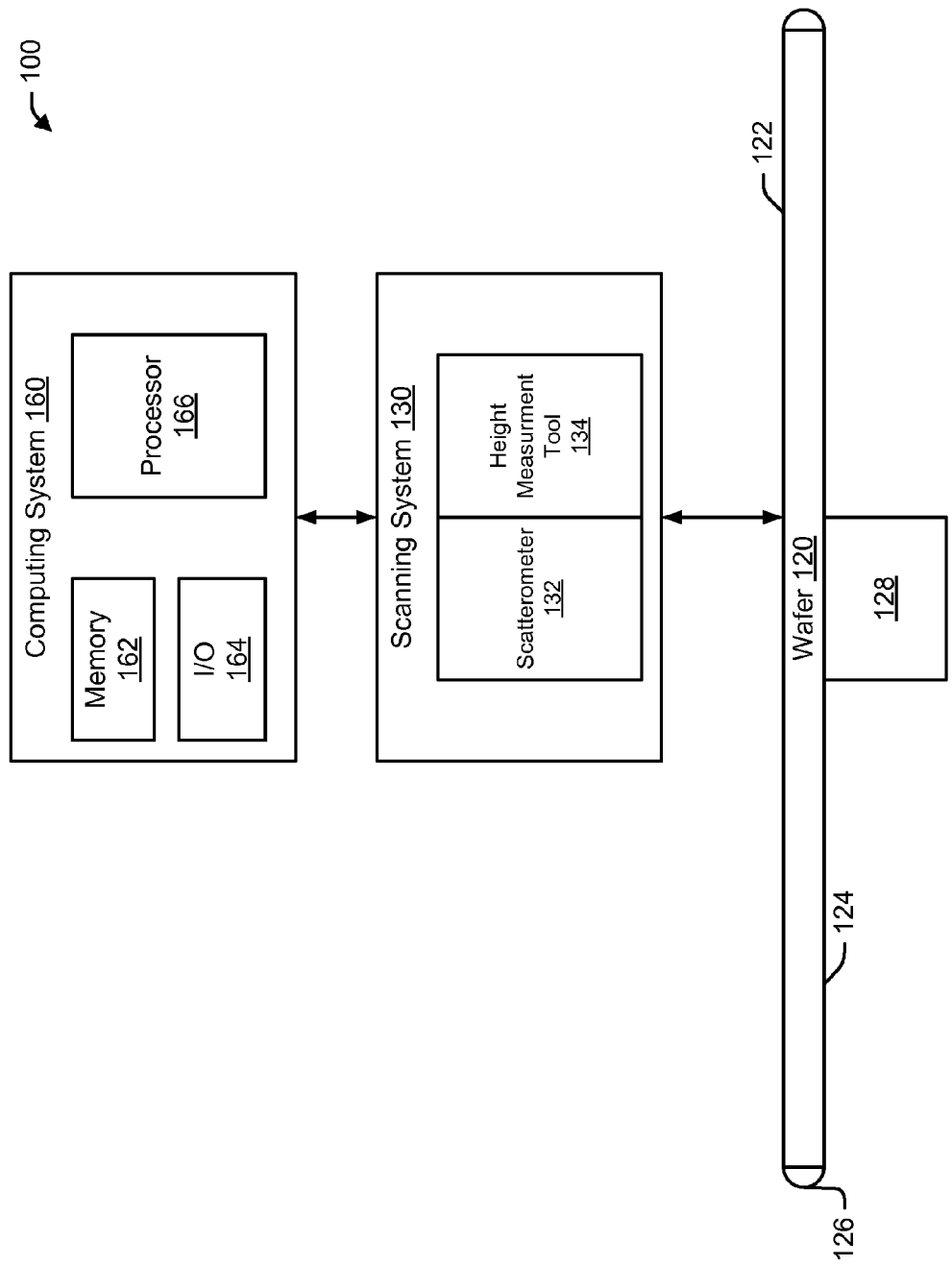
FIG. 1 is a schematic illustration of an embodiment of a system for surface characteristic analysis.

Described herein are exemplary systems and methods for surface characteristic analysis. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

The minimum defect size detectable by dark field (scattered light) optical inspection systems is a function of the wavelength and intensity of radiation used by the inspection system. Commercial optical inspection systems commonly use radiation from coherent light sources such as lasers with a wavelength that measures between 1550 nanometers (nm) and 193 nm, which is from the near infrared to the deep ultraviolet.

Radiation intensity is directly correlated with the output power of the light source and inversely correlated with the spot size of radiation incident on the surface being measured. The output power of a coherent light source is limited by design considerations. Further, it is desirable to maintain the output power of a light source substantially constant during operation. Thus, the intensity of radiation incident on a surface may be varied by changing the spot size of radiation incident on the surface.

Some surface inspection systems, commonly referred to as scatterometers, direct a beam of radiation, commonly in the frequency spectrum of visible light, on the surface of the semiconductor material, then collect and analyze radiation scattered from the surface to quantify characteristics of the surface. Scatterometer inspection systems commonly direct radiation having a relatively large spot size (i.e., between 500 microns and 5 microns). The large spot size permits rapid scanning of surface characteristics, but limits the size of defect which can be detected.

Other surface profile measuring devices may be designed to use small spot sizes. For example, interferometers commonly direct radiation having a relatively small size (i.e., between 5 microns and 0.5 microns). The small spot size permits the detection of very small defects on the surface (e.g., on the order of 1 micron), but requires a prohibitively long time to scan the entire surface of an object.

Embodiments of the surface characteristic analysis system described herein combine a scatterometer and an interferometer in a surface scanning system. The scatterometer provides a large spot size scanner, while the interferometer provides a small spot size scanner. In embodiments, the scatterometer may be used to identify at least one region of the surface considered likely to have defects. The interferometer may then be used to scan the one or more regions identified by the scatterometer to characterize defects in one or more of the identified regions.

FIG. 1 is a schematic illustration of an embodiment of a system for surface characteristic analysis. Referring to FIG. 1, in an embodiment a system 100 comprises scanning system 130 and a computer system 160. The scanning system 130 comprises a scatterometer 132 and a surface profile height measurement tool 134 communicatively coupled to a computing system 160. The scatterometer 132 may be constructed and operated in accordance with the description provided in U.S. Pat. Nos. 6,665,078, 6,717,671, 6,757,056, 6,268,919, 6,229,610, and 6,130,749 to Meeks, et al., the disclosures of which are incorporated herein by reference in their entirety.

In some embodiments the surface profile height 134 may comprise an optical interferometer capable of high-resolution interferometry such as, e.g., a Michelson interferometer, a Fizeau interferometer, a Fabry-Perot interferometer, a Linnik interferometer, a Nomarski interferometer, or the like. In some embodiments the surface profile height measurement tool 134 may comprise an integrating slope sensor, a confocal microscope, a scanning probe microscope, or the like.

The computer system 160 comprises a memory module 162, an input/output module 164 and a processor 166 and may be integrated within system 100 or may be a stand-alone computer system coupled to the system 100.

Wafer 120 includes an upper surface 122, a lower surface 124, and an edge surface 126, which may be substantially flat or curved when viewed in a cross-sectional profile. In the embodiment depicted in FIG. 1, the wafer edge surface is curved when viewed in cross-sectional profile.

During the inspection process a wafer 120 may be rotated about a central axis on a spindle 128, which may be connected to a suitable motor or other drive assembly for inducing rotational motion to the spindle. A drive assembly including, e.g., a motor for moving the scanning system 130 across the surface of the rotating wafer 120 as described herein or as described in U.S. Pat. Nos. 6,665,078, 6,717,671, 6,757,056, 6,268,919, 6,229,610, and 6,130,749, generating data about various characteristics of the surface.

Figure 2:
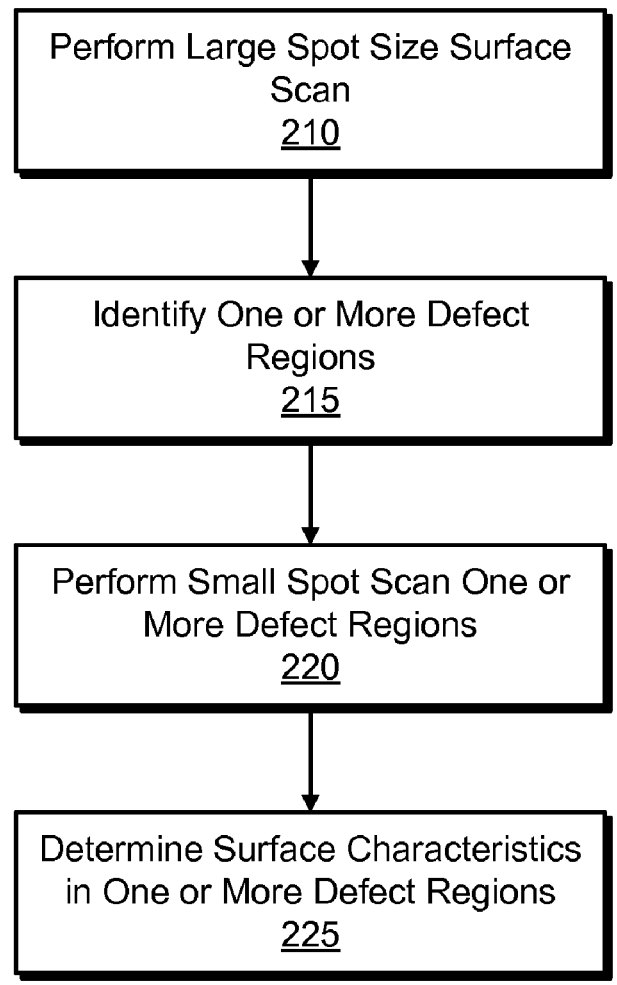
FIG. 2 is a flowchart illustrating operations in an embodiment of a method for surface characteristic analysis.

FIG. 2 is a flowchart illustrating high-level operations in an embodiment of a method for surface characteristic analysis. Referring to FIG. 2, at operation 210 a large spot size surface scan is performed on wafer 120. The large spot size surface scan may be performed with the scatterometer 132. The scan with the scatterometer 132 may identify, at operation 215, one or more defect regions on surface 122. In some embodiments, the location of the defect regions on the surface 122 may be stored in a suitable memory location such as, e.g., in a data file stored in memory module 162 of computer system 160. The location of defect regions may be stored in Cartesian coordinates, polar coordinates, or any other suitable coordinate system.

At operation 220 a small spot size scan is performed on one or more of the defect regions identified in operation 215. The small spot size scan may be performed with the height measurement tool 134.

In some embodiments the height measurement tool 134 may scan all the defect regions identified in operation 215. In other embodiments the interferometer may scan a subset of the defect regions identified in operation 215. For example, in some embodiments the defect regions may be assigned a value indicative of a parameter associated with the defect region. The defect region may be assigned a value indicative of the degree of scattering observed by the scatterometer, the size of the defect region, or of the severity of the defect observed in the defect region. The interferometer may then scan only those defect regions for which the value assigned exceeds a threshold. Alternatively, the interferometer may scan only the top-ranking n defect regions identified in operation 215, where n represents an integer which may be selected as a parameter by a user of the system 100. In some embodiments, n may be an integer between 10 and 20.

At operation 225 surface characteristics in one or more defect regions are determined. In some embodiments the height measurement tool 132 may be used to determine one or more characteristics of the surface such as, e.g., the dimensions (such as height, depth and lateral dimensions) of scratches, pits, particles and the like. The surface characteristics may be stored in a suitable memory location such as, e.g., the memory 162 of computer system 160, and may be presented to a user of a system via a suitable user interface.

Figure 3:
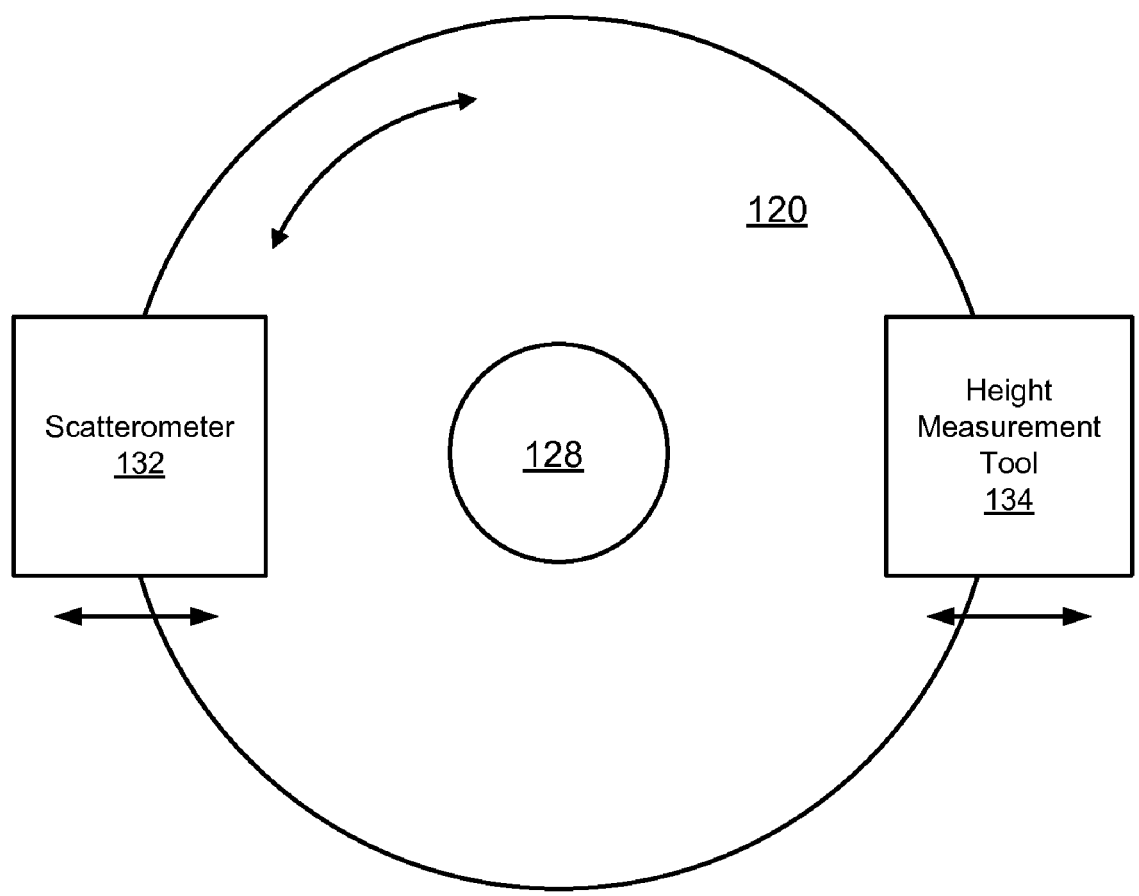
FIG. 3 is a schematic illustration of an arrangement for scanning a surface according to an embodiment.

In some embodiments the scatterometer 132 and the height measurement tool 134 may be constructed as physically distinct sets of optical elements. FIG. 3 is a schematic illustration of an arrangement for scanning a surface in which the scatterometer 132 and the height measurement tool 134 are constructed as separate sets of optics. Referring briefly to FIG. 3, an object such as a magnetic disk substrate 120 may be rotated on a spindle 128, and the scatterometer 132 and height measurement tool 134 may be moved in a radial direction across the surface of disk substrate 120.

In an embodiment in which the scatterometer 132 and the height measurement tool 134 are constructed from separate optics assemblies the scatterometer 132 and measurement tool 134 may utilize radiation sources having the same wavelength or having different wavelengths. In addition, the scatterometer 132 and the height measurement tool 134 may move in a coordinated fashion or may move independently.

Figure 4A:
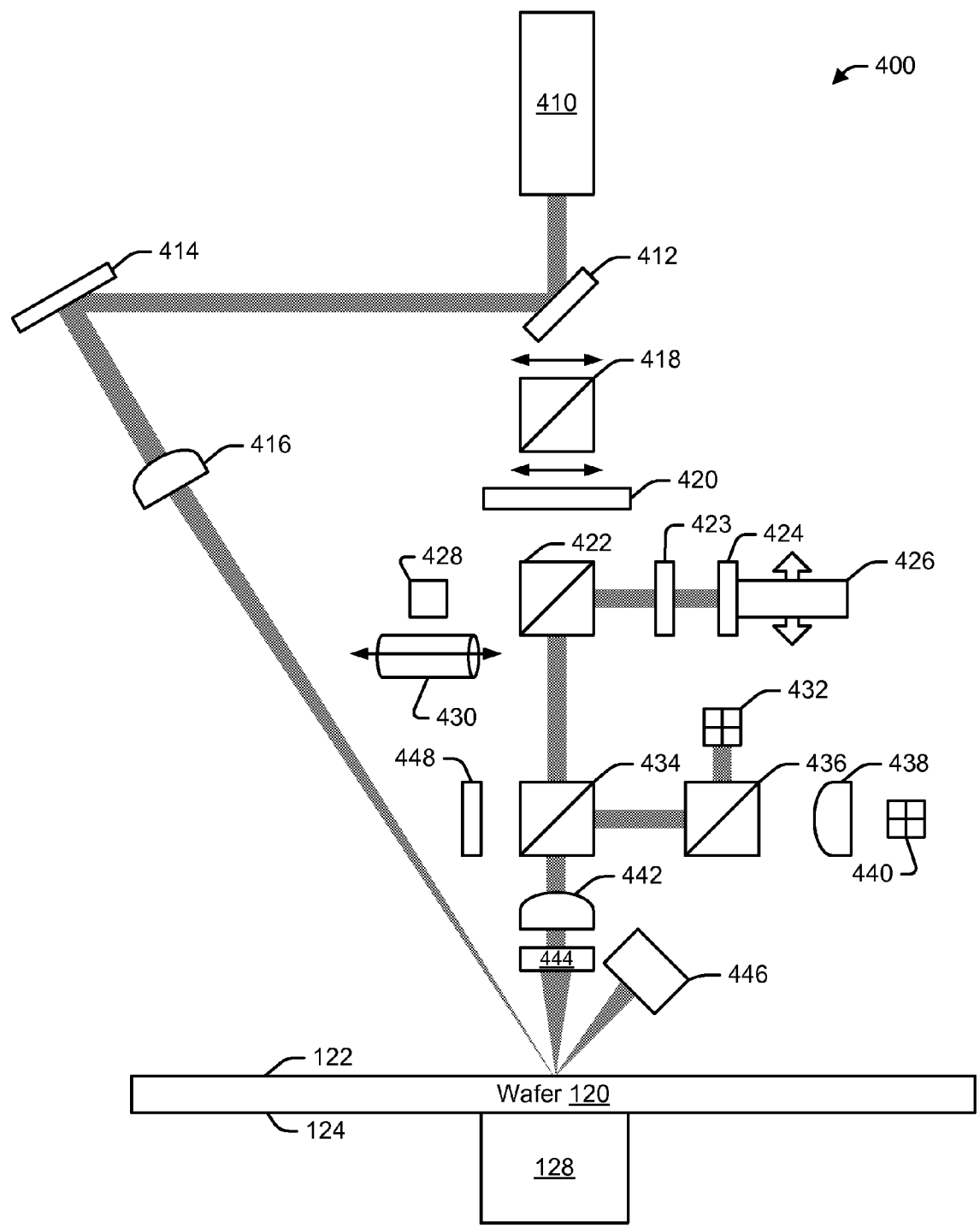
FIGS. 4A and 4B are schematic illustrations an embodiment of an apparatus for scanning a surface according to an embodiment.
Figure 4B:
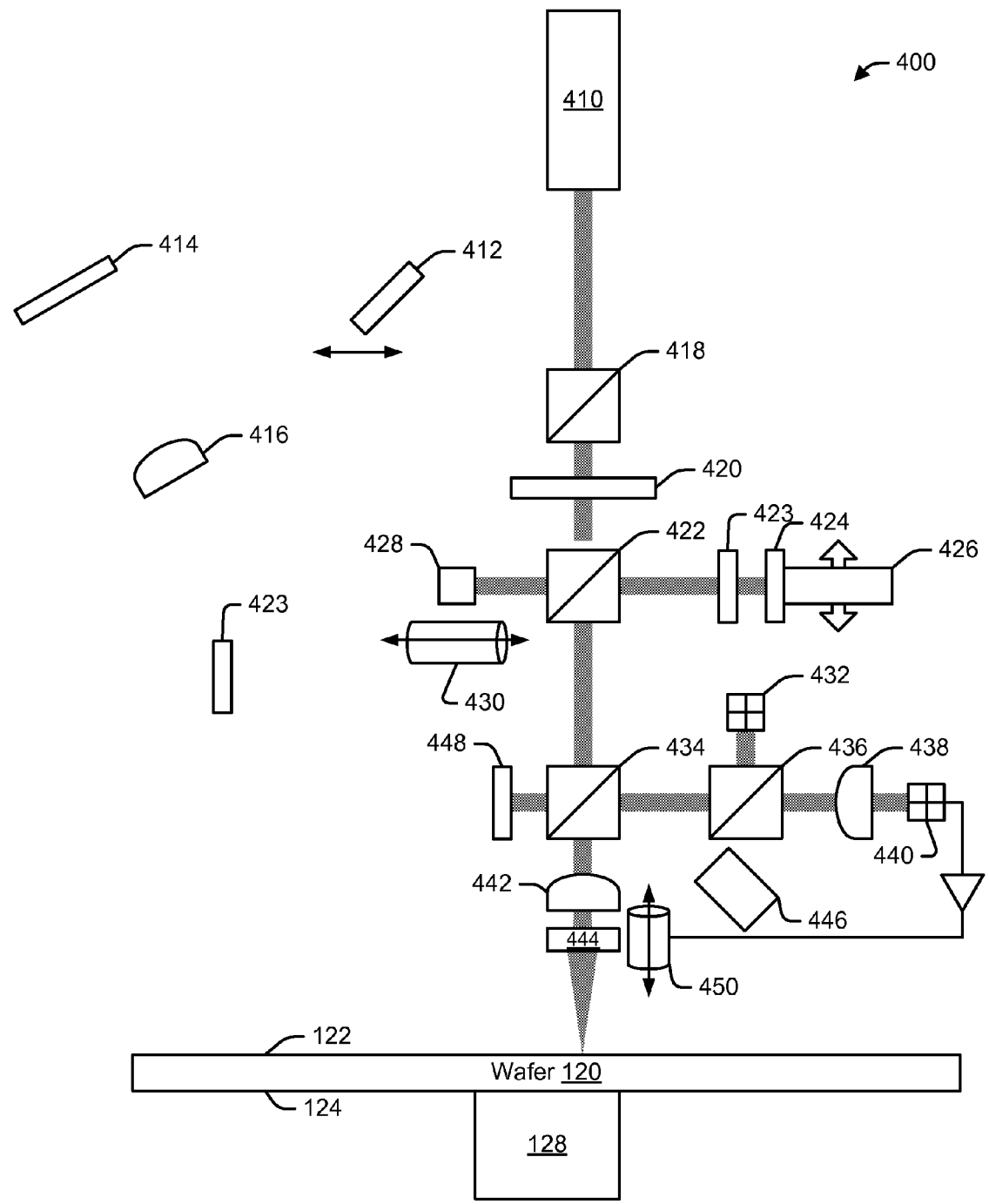

In some embodiments the scatterometer 132 and the height measurement tool 134 may be constructed as a single physical component that shares one or more optical elements. For example, FIGS. 4A and 4B are schematic illustrations an embodiment of an apparatus for scanning a surface according to an embodiment. The embodiment depicted in FIGS. 4A and 4B includes optical assemblies to implement a scatterometer and an interferometer, and utilizes a mirror moveable between a first position in which the scatterometer is active and a second position in which the interferometer is active.

Referring first to FIG. 4A, in one embodiment surface analyzer assembly 400 uses a multi-mode, multi-wavelength laser diode 410 which is available from Rohm Co., LTD Kyoto, Japan as model number RLD-78MV. The radiation may be of any wavelength. In one embodiment a 405 nm violet source available from Coherent, Inc. may be implemented. In another embodiment a 635 nm source may be implemented. Assembly 400 further includes a mirror 412 moveable between a first position in which the scatterometer optics are active and a second position in which the interferometer optics are active.

Assembly 400 further includes a turning mirror 414 and a focusing lens 416, which form a portion of the light directing assembly when the assembly 400 is operated in scatterometer mode. Assembly 400 further includes a polarizing beam splitter 418, a quarter wave plate 420, beam splitters 422, 434, focusing lens 442 and flat glass window 444, which form a portion of the light directing assembly when the assembly 400 is operated in interferometer mode. Focusing lens 442 and window 442 are mounted on a mechanical actuator that allows it to move closer or farther from wafer 420.

Assembly 400 further includes a beam splitter 436 and quadrant detectors 432, 440, which form a portion of the light receiving assembly when the assembly 400 is operated in interferometer mode. An astigmatic focusing lens 438 is positioned in the optical path between the beam splitter 436 and the quadrant detector 440. Quadrant detector 432 forms a portion of the light receiving assembly when the assembly 400 is operated in scatterometer mode.

Assembly 400 further includes a retroreflector 428 (its type can be solid glass retroreflector, or hollow retroreflector, or a "lens and mirror assembly"). The retroreflector is mounted on an actuator 430 that allows to increase or decrease its distance to beamsplitters 422. Finally, assembly 400 also includes a photodetector 424 providing a signal 426 that will be used for adjusting the position of retroreflector 428.

Operation of assembly 400 in scatterometer mode will be explained with reference to FIG. 4A. Radiation emitted from laser diode 410 is reflected from mirror 412 onto a turning mirror 414, which redirects the radiation toward a focusing lens 416, which in turn focuses the radiation onto the surface 122 of wafer 120. As described above, the scatterometer assembly may focus radiation into a spot size that measures between 500 microns and 5 microns in size.

A portion of the radiation scattered from surface 122 of wafer 120 is incident on flat glass 444 and focusing lens 442, which in turn directs the scattered radiation onto a beam splitter 434. Beam splitter 434 directs a portion of the radiation onto a beam splitter 436, which in turn directs a portion of the radiation onto quadrant detector 432. Another portion of the radiation incident on beam splitter 434 is transmitted through beam splitter 434 to beam splitter 422, which directs the radiation to detector 424. The outputs from the detectors 424 and 432 are digitized by a conventional analog to digital converter and directed to the memory module 162 of computer system 160. The data generated from the output of quadrant detectors 424, 432, and/or 440 may then be analyzed by the personal computer to detect a defect region in the surface 122 of wafer 120. The location of the defect region may be recorded in memory 162 of computer system 160.

Operation of assembly 400 in interferometer mode will be explained with reference to FIG. 4B. In interferometer mode, mirror 412 is moved to a second position such that radiation emitted from laser diode 410 bypasses mirror 412 and is directed onto beam splitter 418. Radiation transmitted through the polarizing beam splitter 418 is transmitted through a quarter wave plate 420 that converts its linear polarization into circular polarization. The purpose of using the polarizing beamsplitters 418 and quarter-wave plate 420 combination is that to isolate the laser diode from the light back-reflected from the wafer 120, that could otherwise affect the stability of the radiation emitted. Upon traveling back up through the quarter-wave plate 420. The returning circularly polarized light is converted into light linearly polarized in a direction perpendicular to what it was on the way down to wafer 120. It will thus be reflected almost entirely to the side of polarizing beam splitter 418, thereby optically isolating laser diode 410.

Beam splitter 422 diverts a portion of the beam to retroreflector 428, which retro-reflects the beam onto detector 424. This beam can be referred to as the reference beam, and its optical path length can be controlled by moving actuator 430.

Radiation emitted from beam splitter 422 is directed to beam splitter 434, which directs a portion of the beam onto detector 448. Detector 448 thus measure a light intensity proportional to the light intensity sent to wafer 420. Radiation emitted from beam splitter 434 passes through lenses 442 and 444, which focus the beam into a small spot (e.g., 0.5 microns to 5 microns) onto the surface 122 of wafer 120.

Radiation reflected from the surface 122 of wafer 120 passes through lenses 444 and 442 onto beam splitter 434, which directs a portion of the reflected radiation onto beam splitter 436, which in turn directs a portion of the radiation onto quadrant detectors 432 and 440. Detector 432 is used to measure the beam shift upon reflection on wafer 120, which is proportional to the local slope of the topography of wafer 120. The use of a quadrant detector allows to measure said slope in the X and Y directions, and to estimate the topography of the wafer by integration of those slopes into a displacement. In that embodiment, it is implemented as an additional small spot height sensor, complementary to the interferometer subsystem. Detector 440 is used for the purpose of auto-focusing the light: in a small spot system such as described here, the depth of focus of the system (i.e., the range of distances to the wafer 120 the system can work at) is very limited, to say 1 micron or so. Such system would thus not be able to function with the typical disks runouts while spinning, on the order of 10 microns or so, without the addition of an auto-focus capability. In this embodiment, the detector 440 measures the aspect ratio of the ellipse formed by the astigmatic lens 438. The nominal focus is when the ellipse has an aspect ratio of 1 (circle), while it takes opposite aspect ratios when the wafer 120 is above or below focus. The signals from the quad-detector 440 are combined to form a "focus error signal" that is used in a feedback loop to create the desired "auto-focus" functionality by finely controlling actuator 450.

Radiation reflected from disk (or wafer) 120 and propagating straight through beam splitter 434 is then directed by beam splitter 422 and focused by a lens 423 onto detector 424, onto the same spot as the light from the reference beam (reflected off of retroreflector 428). The coherent sum of those two beams yields the interference signal measured by detector 424. Focusing through a lens onto detector 424 removes the sensitivity to the angle of the topography on wafer 120 that would otherwise shift the beams and change the efficiency of the interference. The signal 426 from light sensor 424 is used for two purposes. The first is to give a fairly low frequency (i.e., less than about 2 kHz) feedback signal allowing to move actuator 430 (and thus retroreflector 428) to maintain the respective phase difference between the internal reference beam and the beam reflected from wafer 120 at 90 degrees (quadrature). This in turn allows the interferometer to be at its best sensitivity (light level change per nm of displacement) to measure the small defects of interest. The second purpose of the interferometer signal 426 is to yield the high frequency (i.e., greater than about 50 kHz) signature of a small defect passing under the beam. For example, at 4 kRPm and 1" radius, a 200 micron wide defect will typically yield an interference signal at 50 kHz and above. This places it out of the mechanical frequency range, and thus measure small enough defects accurately. For this method to work best, the defects range of height should be well within one quarter of the wavelength use, e.g. +40 nm to −40 nm for a 405 nm wavelength.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. An inspection system for inspecting a substrate, the inspection system comprising:

a radiation beam source for producing a radiation beam, first optical elements for selectively diverting the radiation prior to the radiation beam impinging upon the substrate, the inspection system being in a scatterometer mode when the radiation beam is diverted in a first direction, and the inspection system being in an interferometer mode when the radiation beam is diverted in a second direction, second optical elements for receiving the radiation beam only when the inspection system is in scatterometer mode, and for directing and focusing the radiation beam onto the substrate at a non-perpendicular angle to a surface of the substrate, a first sensor for receiving the radiation beam as it is reflected from the substrate only when the inspection system is in scatterometer mode, and for making scatterometry measurements, third optical elements for receiving the radiation beam prior to the radiation beam impinging upon the substrate only when the inspection system is in interferometer mode, and for directing and focusing the radiation beam onto the substrate at a perpendicular angle to the surface of the substrate, fourth optical elements for diverting the radiation beam along two light paths when the inspection system is in interferometer mode, the second optical elements also for rejoining the two light paths after a first of the two light paths has reflected the radiation beam off of the substrate and a second of the two light paths has reflected the radiation beam off of a reference surface, and a second sensor for receiving the rejoined radiation beam when the inspection system is in interferometer mode, and for making interferometry measurements, where the first sensor and the second sensor are two separate sensors, and the first optical elements, the second optical elements, the third optical elements, and the fourth optical elements are all separate optical elements.

2. The inspection system of claim 1, further comprising fifth optical elements for directing the radiation beam after it has been reflected off of the substrate, in both the scatterometer mode and the interferometer mode, onto a quadrant sensor.

* * * * *